United States Patent
Pfaeffli et al.

(10) Patent No.: US 6,221,870 B1
(45) Date of Patent: Apr. 24, 2001

(54) ERGOLINE DERIVATIVES AND THEIR USE AS SOMATOSTATIN RECEPTOR ANTAGONISTS

(75) Inventors: Paul Pfaeffli, Oberwil; Peter Neumann, Bern; Robert Swoboda, Koeniz, all of (CH); Peter Stütz, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/424,377

(22) PCT Filed: May 27, 1998

(86) PCT No.: PCT/EP98/03125

§ 371 Date: Nov. 23, 1999

§ 102(e) Date: Nov. 23, 1999

(87) PCT Pub. No.: WO98/54183

PCT Pub. Date: Dec. 3, 1998

(30) Foreign Application Priority Data

May 29, 1997 (GB) .................................................. 9711043

(51) Int. Cl.⁷ ........................ A61K 31/496; C07D 401/14
(52) U.S. Cl. ............................... 514/253.02; 514/253.02; 544/361
(58) Field of Search ........................ 514/253.02; 544/361

(56) References Cited

U.S. PATENT DOCUMENTS

| 3,583,991 | * | 6/1971 | Troxler et al. | 260/268 |
| 3,592,816 | | 7/1971 | Troxler et al. | 260/268 |
| 4,196,288 | * | 4/1980 | Beacco et al. | 544/125 |
| 4,728,649 | * | 3/1988 | Mantegani et al. | 514/253 |

FOREIGN PATENT DOCUMENTS

| 1188197 | 4/1990 | (GB) . |
| 1345546 | 1/1974 | (HU) . |
| WO 97 03054 | 1/1997 | (WO) . |

OTHER PUBLICATIONS

Nordmann R. et al., Journal of Medicinal Chemistry, vol. 28, No. 3, pp. 367–375(1985).
Derwent Abstract, 86–271902/42 (corresponds to (EP 197, 241–A) Oct./1986.
Derwent Abstract, 0006972 (corresponds to (Belg. 625369), 1966.
Derwent Abstract 77084W/47 (corresponds to (Belg. 828, 735) Nov./1975.

* cited by examiner

Primary Examiner—Mukund J. Shah
Assistant Examiner—Ben Schroeder
(74) Attorney, Agent, or Firm—Joseph J. Borovian

(57) ABSTRACT

The invention provides compounds of formula I

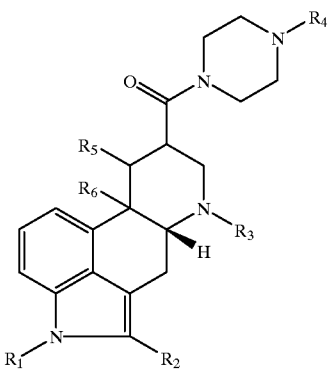

wherein $R_1$ to $R_6$ are as defined in the description, and a process for preparing them. The compounds of formula I are useful as pharmaceuticals.

7 Claims, No Drawings

ERGOLINE DERIVATIVES AND THEIR USE AS SOMATOSTATIN RECEPTOR ANTAGONISTS

The present invention relates to novel ergoline derivatives, their preparation, their use as pharmaceuticals and pharmaceutical compositions comprising them.

More particularly the present invention provides a compound of formula I

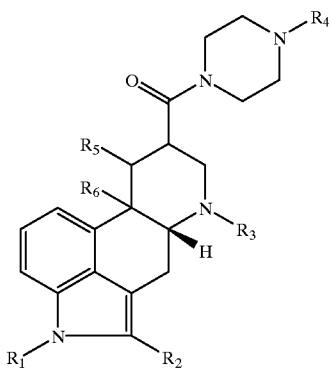

I wherein $R_1$ is hydrogen, $(C_{1-4})$akyl or a group of formula

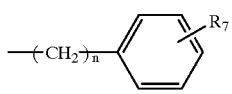

(a)

wherein n is 1 to 4 and $R_7$ is fluorine, chlorine, hydroxy, $(C_{1-4})$alkyl or $(C_{1-4})$alkoxy, $R_2$ is hydrogen, chlorine, bromine, iodine, $(C_{1-4})$alkyl or $(C_{1-4})$alkylthio, $R_3$ is hydrogen or $(C_{1-4})$alkyl, $R_4$ is (i) a group of formula

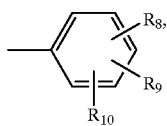

(b)

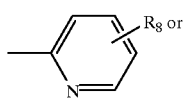

(c)

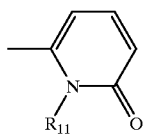

(d)

wherein $R_8$ is fluorine, chlorine, nitro or cyano, $R_9$ and $R_{10}$ independently, are hydrogen, fluorine, chlorine, nitro or cyano and $R_{11}$ is $(C_{1-4})$alkyl or $(C_{2-5})$alkenyl, or (ii) a group of formula

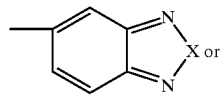

(e)

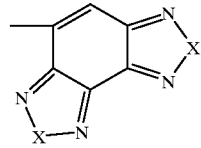

(f)

wherein each X independently is O or S, and $R_5$ and $R_6$ are each hydrogen or form together a further bond between the two carbon atoms on which they are located, provided that $R_8$ is not 4-$NO_2$ if $R_1$, $R_2$, $R_9$ and $R_{10}$ are hydrogen, $R_3$ is methyl and $R_5$ and $R_6$ form together a further bond between the two carbon atoms on which they are located, and that $R_8$ is not chlorine if $R_1$, $R_2$, $R_9$ and $R_{10}$ are hydrogen and $R_3$ is methyl, in free base or acid addition salt form.

The invention includes the enantiomers as well as their mixtures, e.g. the epimeric or racemic mixtures which may be present on account of the asymmetrical carbon atoms in positions 5, 8 and 10. The configuration [5R,10R] is preferred (5R corresponding to a 5β hydrogen). The configuration 8β is also preferred.

The above-defined alkyl, alkoxy and alkylthio groups preferably represent methyl, methoxy and methylthio.

In a further aspect, the invention provides a process for the production of the compounds of formula I and their acid addition salts, whereby a compound of formula II

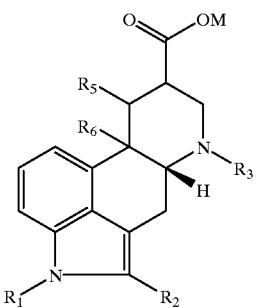

II wherein $R_1$, $R_2$, $R_3$, $R_5$ and $R_6$ are as defined above and M is H or an alkali metal, is reacted with a compound of formula III

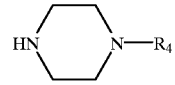

III wherein $R_4$ is as defined above, and the compounds of formula I thus obtained are recovered in free base or acid addition salt form.

The reaction can be effected according to known amide formation methods, for example as described in Example 1. In formula II, M as an alkali metal is for example sodium.

Working up the reaction mixtures obtained according to the above process and purification of the compounds thus obtained may be carried out in accordance to known procedures.

Acid addition salts may be produced from the free bases in known manner, and vice versa. Suitable acid addition salts for use in accordance with the present invention include for example the hydrochloride.

The starting compounds of formula III may be produced by reacting piperazine with a compound of formula $R_4$—Cl, e.g. as described in Example 1.

The compounds of formulae II and $R_4$—Cl are known or may be produced in analogous manner to known procedures.

Compounds of the invention, e.g. compounds of formula I and their pharmaceutically acceptable acid addition salts, hereinafter referred to as agents of the invention, exhibit interesting pharmacological properties when tested in vitro using SRIF receptor expressing cell cultures and in animals, and are therefore useful as pharmaceuticals.

In particular the agents of the invention bind to somatostatin receptors. More particularly they are selective antagonists at Somatostatin $sst_1$ receptors, previously called SSTR-1 receptors (see Hoyer et al., TIPS, 1995, 16; 86–88), as determined in radioligand binding and second messenger studies [see for example K Kaupmann et al., FEBS LETTERS 1993, 331: 53–59].

The agents of the invention are therefore useful for treatment in anxiety, depression, schizophrenia, neurodegenerative diseases such as dementia, for the treatment of tumors and for vascular disorders and immunological diseases.

The usefulness of the agents of the invention in these indications is confirmed in a range of standard tests as indicated below:

At doses of about 0.3 to 3 mg/kg p.o., the agents of the invention increase exploratory behavior of mice in the open half of the half enclosed platform, a model which is predictable for anxiolytic activity (Psychopharmacology, 1986, 89:31–37).

In the same half enclosed platform model, the agents of the invention at the above indicated doses also increase vigilance of the mice. The compounds are therefore indicated for the treatment of depression, schizophrenia and dementia, in particular of senile dementia of the Alzheimer type (SDAT).

In the intruder mouse test [Triangle, 1982, 21:95–105; J. Clin. Psychiatry, 1994, 55:9 (suppl. B) 4–7], the agents of the invention increase non-social behavior, social investigation and sex, and reduce defensive ambivalence in the treated intruder mouse at doses of about 1 to about 10 mg/kg s.c., suggesting an antidepressant profile like carbamazepine and lithium, a neuroleptic profile like clozapine and an anxiolytic profile like diazepam.

Furthermore at about 3 to about 30 mg/kg p.o. the agents of the invention reduce aggressive behavior (attacks, chases, bites) in the Matched Pairs Situation test in mice [Dixon et al., J. Clin. Psychiatry 55: (9) [Suppl. B] 4–7 (1994)]. Since as mentioned above they additionally attenuate defensive behaviors in the intruder mouse test, the compounds of the invention exhibit an ethopharmacological profile which is very similar to that of carbamazepine, lithium chloride and clozapine. They are therefore indicated for the treatment of affective disorders including bipolar disorders e.g. manic-depressive psychoses, extreme psychotic states e.g. mania, schizophrenia, and excessive mood swings where behavioral stabilization is desired. In addition, the compounds are indicated in anxiety states, generalized anxiety as well as social and agoraphobia, as well as those behavioral states characterized by social withdrawal e.g. negative symptoms.

In addition, the agents of the invention improve the performance in the step-down passive avoidance paradigm in mice following both pre- (p.o.) and post-trial (i.p.) adrn-nistration of about 0.01 to about 10 mg/kg, enhance retrieval-performance in the step-through passive avoidance test (p.o.) [Mondadori et al., Behav. Neural. Biol. 60: 62–68 (1993)] and partially counteract electroshock-induced amnesia (p.o.) [Mondadori et al., Physiol. & Behav. 18: 1103–1109 (1997)]. Finally the agents specifically enhance social recognition of familiar, but not unfamiliar juvenile rats at doses of about 0.03 to about 3 mg/kg p.o. These findings indicate that the agents facilitate learning and memory at low doses. These features combined with the marked anti-aggressive properties and sociotropic effects suggest that the agents of the invention are effective in the treatment of attention deficit and hyperactivity disorders (ADHD).

The agents of the invention are also effective in the treatment of various kinds of tumors, particularly of $sst_1$ receptor bearing tumors, as indicated in proliferation tests with various different cancer cell lines and in tumor growth experiments in nude mice with hormone dependent tumors [see for example: G. Weckbecker et al., Cancer Research 1994, 54: 6334–6337]. Thus the compounds are indicated in the treatment of, for example, cancers of the breast, the prostate, the colon, the pancreas, the brain and the lung (small cell lung cancer).

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.25 to about 50 mg of an agent according to the invention.

The agents of the invention may be administered by any conventional route, for example parenterally e.g. in form of injectable solutions or suspensions, or enterally, preferably orally, e.g. in the form of tablets or capsules, or nasally.

For all above indications the preferred compound is the compound of example 1 below. Said compound has high affinity for native rat $sst_1$ receptors ($pIC_{50}$=9.7) and native and recombinant human $sst_1$ receptors ($pIC_{50}$=9.0 and 8.8 respectively), without significant activity for a wide range of neurotransmitter receptors. At 3–30 mg/kg p.o., the compound clearly lowers aggressive behavior in the above-mentioned Matched Pairs Situation test and reverses social withdrawal in the above-mentioned intruder mouse test. These effects are also observed with the standard anti-manic drugs lithium and carbamazepine at 3–30 mg/kg s.c., indicating similar therapeutic effects in man. However, lithium and carbamazepine were found to be less potent and are known to have considerable drawbacks such as a narrow therapeutic window and slow onset of action.

The preferred indications are depression, anxiety, affective disorders, including bipolar disorders, e.g. mania, and ADHD.

In accordance with the foregoing, the present invention also provides an agent of the invention for use as a pharmaceutical, e.g. for the treatment of depression, anxiety, bipolar disorders and ADHD.

Moreover the present invention provides an agent of the invention, for the manufacture of a medicament for the treatment of any condition mentioned above, e.g. depression, anxiety, bipolar disorders and ADHD.

In still a further aspect the present invention provides a method for the treatment of any condition mentioned above, e.g. depression, anxiety, bipolar disorders and ADHD in a subject in need of such treatment, which comprises administering to such subject a therapeutically effective amount of an agent of the invention.

The following examples illustrate the invention. The temperatures are given in degrees Celsius and are uncorrected.

EXAMPLE 1

[5R, 8R, 10R]-2-Bromo-9,10-dihydro-lysergic-acid-4-(1-methyl-1H-pyrid-6-on-2-yl)-piperazine-amide a) 2-Chloro-1-methyl-pyrid-6-one 51.82 g of 2-chloro-pyrid-6-one (400 mmol) and 12.7. g of 83% sodium-hydride dispersion in mineral oil (440 mmol) are reacted in 400 ml absolute dimnethylfomamide at room temperature under argon for 15 minutes. 32.4 ml methyl-iodide (520 mmol) are added dropwise and stirring is continued at 50° for 5 hours. The reaction mixture is evaporated on a rotary evaporator until the solvent starts to distill from a bath of 60°.

b) 4-(1-methyl-1H-pyrid-6-on-2-yl)-piperazine

The crude solution of 2-chloro-1-methyl-pyrid-6-one obtained under a) is mixed with 103 g piperazine (1.2 mol) and reacted at 110° for 6 hours. The solvent is removed on a rotary evaporator at 70° under 0.01 Torr. Removal of the excess of piperazine is effected by partitioning between 16% natrium chloride in water and toluene/1-propanol—50/50. The title compound is crystallized as hydrogen-oxalate salt from 2-propanol and as free base from toluene. Mp=108°.

c) [5R, 8R, 10R]-2-Bromo-9,10-dihydro-lysergic-acid-4-(1-methyl-1H-pyrid-6-on-2-yl)-piperazine-amide 2.794 g (8 mmol) of [5R, 8R, 10R]-2-Bromo-9,10-dihydro-lysergic-acid are suspended in 19.1 ml 38% propane-phosphonic-acid anhydride in dimethylformamide (24 mmol) and 8 ml absolute pyridine, and stirred for 15 minutes at room temperature. After addition of 1.546 g 4-(1-methyl-1H-pyrid-6-on-2-yl)-piperazine (8 mmol), stirring is continued overnight. The reaction mixture is partitioned between toluene/2-propanol—60/40 and 2 M aqueous ammonia, the organic layer evaporated and chromatographed on 24 g silicagel with toluene/ethanol/conc. aqueous ammnonia—90/0.9/0.1. The main component is recrystallized from ethyl-acetate. Mp=250–253° (decomposition); $[\alpha]_{D,20} = -94.3°$ (0.5% in dimethylformamide).

The compounds of formula I defined below and in which the configuration is [5R,8R,10R] are produced in analogous manner to example 1.

In the following compounds, $R_5$ and $R_6$ are hydrogen.

| Ex. | $R_1$ | $R_2$ | $R_3$ | $R_4$ | Mp | $[\alpha]_{D,20}$** |
|---|---|---|---|---|---|---|
| 2 | H | | Cl | $CH_3$ | (c); $R_8$ = H | 210* | −99.7 |
| 3 | " | | H | " | (d); $R_{11}$ = $CH_3$ | 250* | −66.0 |
| 4 | (a); n = 1, $R_7$ = 4-F | Cl | " | (c); $R_8$ = H | amorph. | −64.6 |
| 5 | (a); n = 3, $R_7$ = 4-F | " | " | " | | −54.2 |
| 6 | H | Br | " | " | 181 | −54.5 |
| 7 | " | " | H | H | " | 230* | −46.2 |
| 8 | " | " | Br | " | " | 166* | −40.1 |
| 9 | (a); n = 1, $R_7$ = 4-F | " | " | $CH_3$ | " | amorph. | −56.9 |
| 10 | H | | " | $CH_3$ | " | 135 | −102.5 |

-continued

| Ex. | $R_1$ | $R_2$ | $R_3$ | $R_4$ | Mp | $[\alpha]_{D,20}$** |
|---|---|---|---|---|---|---|
| 11 | " | $SCH_3$ | " | " | 130 | −101.7 |
| 12 | (a); n = 1, $R_7$ = 2-$CH_3$ | Br | " | " | 111 | −88.4 |
| 13 | H | " | butyl | " | 121 | −84.3 |
| 14 | (a); n =1, $R_7$ = 4-F | $CH_3$ | $CH_3$ | " | amorph. | −93.2 |
| 15 | H | H | " | (b); $R_8$ = 4-$NO_2$; $R_9$ = $R_{10}$ = H | 240 | −105.6 |
| 16 | " | $CH_3$ | " | " | 170 | −104.3 |
| 17 | " | H | " | (d); $R_{11}$ = H | 260* | −96.9 |
| 18 | " | Br | H | (d); $R_{11}$ = $CH_3$ | 260* | −66.9 |
| 19 | " | " | $CH_3$ | (b); $R_8$ = 4-$NO_2$; $R_9$ = $R_{10}$ = H | 174 | −89.5 |
| 20 | " | Cl | " | " | 171 | −95.6 |
| 21 | " | " | " | (d); $R_{11}$ = $CH_3$ | 272* | −102.8 |
| 22 | " | " | " | (f); both X's = O | 296 | −89.6 |
| 23 | " | " | " | (d); $R_{11}$ = allyl | 250* | −89.9 |
| 24 | " | Br | " | " | 190*** | |
| 25 | " | " | " | (e); X = O | 267 | −90.0 |

In the following compound $R_5$ and $R_6$ form together a further bond:

| 26 | " | $CH_3$ | " | " | 162 | +7.4 |

*decomposition
**°(0.5% in DMF)
***hydrochloride

What is claimed is:

1. A compound of formula I

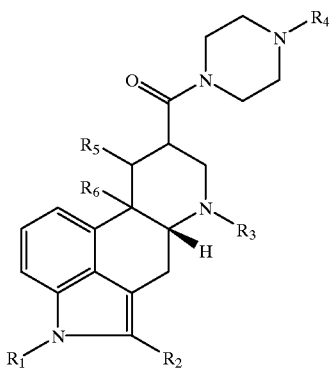

I wherein

R₁ is hydrogen, (C₁₋₄)alkyl or a group of formula

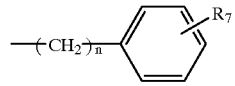 (a)

wherein n is 1 to 4 and R₇ is fluorine, chlorine, hydroxy, (C₁₋₄)alkyl or (C₁₋₄)alkoxy, R₂ is hydrogen, chlorine, bromine, iodine, (C₁₋₄)alkyl or (C₁₋₄) alkylthio, R₃ is hydrogen or (C₁₋₄)alkyl, R₄ is (i) a group of formula

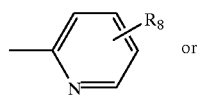 (c)

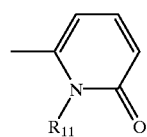 (d)

wherein R₈ is fluorine, chlorine, nitro or cyano and R₁₁ is (C₁₋₄)alkyl or (C₂₋₅)alkenyl, or (ii) a group of formula

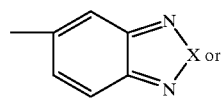 (e)

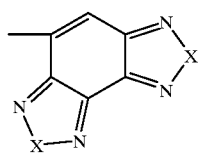 (f)

wherein each X independently is O or S, and

R₅ and R₆ are each hydrogen or form together a further bond between the two carbon atoms on which they are located, in free base or acid addition salt form.

2. A compound of formula I according to claim 1 wherein R₄ is a group of formula (d), in free base or acid addition salt form.

3. A compound of formula I according to claim 1 wherein R₄ is a group of formula (e), in free base or acid addition salt form.

4. A process for the production of a compound of formula I as defined in claim 1, or a salt thereof, which includes the step of reacting a compound of formula II

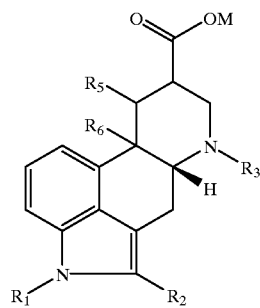 II wherein R₁, R₂, R₃, R₅ and R₆ are as defined in claim 1 and M is H or an alkali metal, with a compound of formula III

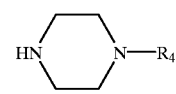 III wherein R₄ is as defined in claim 1, and recovering the so obtained compound of formula I in free base or acid addition salt form.

5. A pharmaceutical composition comprising a compound according to claim 1 in free base or pharmaceutically acceptable acid addition salt form, in association with a pharmacetuical carrier or diluent.

6. A method for the treatment of depression, anxiety, bipolar disorders and ADHD in a subject in need of such treatment, which comprises administering to such subject a therapeutically effective amount of a compound according to claim 1 in free base or pharmaceutically acceptable acid addition salt form.

7. A compound of formula Ia

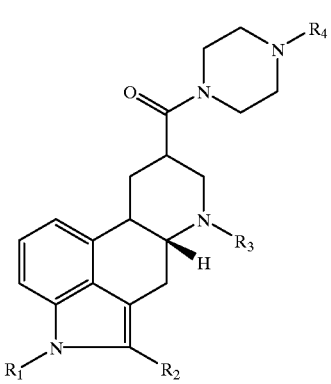 Ia wherein R₁ is hydrogen or a group of formula a)

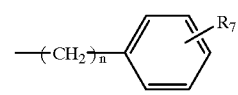 a)

where n is 1 to 3 and $R_7$ is fluoro or $(C_{1-4})$ alkyl;
$R_2$ is hydrogen, chloro, bromo, $(C_{1-4})$ alkyl or $(C_{1-4})$ alkylthio;
$R_3$ is hydrogen or $(C_{1-4})$ alkyl; and
$R_4$ is a group of formula
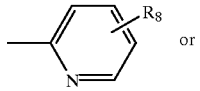 (c)
or
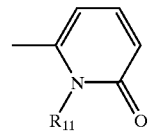 (d)
where $R_8$ is hydrogen, and $R_{11}$ is $(C_{1-4})$ alkyl; in free base or acid addition salt form.
* * * * *